United States Patent
Yoko et al.

(10) Patent No.: US 8,556,900 B2
(45) Date of Patent: Oct. 15, 2013

(54) SURGICAL INSTRUMENT FOR IMPACTING AND EXTRACTING A CUTTING INSTRUMENT

(75) Inventors: Tim Yoko, Granger, IN (US); Brian E. Roach, Osceola, IN (US); Vijayraj G. Nangli, Karnataka (IN)

(73) Assignee: Zimmer, Inc., Warsaw, IN (US)

( * ) Notice: Subject to any disclaimer, the term of this patent is extended or adjusted under 35 U.S.C. 154(b) by 95 days.

(21) Appl. No.: 13/309,140

(22) Filed: Dec. 1, 2011

(65) Prior Publication Data

US 2013/0144296 A1 Jun. 6, 2013

(51) Int. Cl.
*A61B 17/17* (2006.01)

(52) U.S. Cl.
USPC .................................. 606/84; 606/79; 606/88

(58) Field of Classification Search
USPC ....... 606/79, 84, 86 R, 88; 623/20.34; 407/13
See application file for complete search history.

(56) References Cited

U.S. PATENT DOCUMENTS

| | | | |
|---|---|---|---|
| 43,909 A | * | 8/1864 | Hair .............................. 606/175 |
| 5,282,866 A | * | 2/1994 | Cohen et al. ............... 623/20.34 |
| 5,634,927 A | | 6/1997 | Houston et al. |
| 5,665,090 A | | 9/1997 | Rockwood et al. |
| 7,344,542 B2 | | 3/2008 | Collazo et al. |
| 7,390,327 B2 | | 6/2008 | Collazo et al. |
| 2004/0249384 A1 | | 12/2004 | Blaha et al. |
| 2008/0183177 A1 | | 7/2008 | Fox et al. |

OTHER PUBLICATIONS

Zimmer NexGen LPS Fixed Knee Surgical Technique, Zimmer, Inc., 2002, 2008, 44 pages.
Zimmer NexGen CR-Flex and LPS-Flex Knees Surgical Technique with Posterior Referencing Instrumentation, Zimmer, Inc. 2010, 2011, 48 pages.
Zimmer NexGen MIS Modular Tibial Plate and Keel Cemented Surgical Technique, Zimmer, Inc., 2006, 2011, 26 pages.
Zimmer NexGen MIS Tibial Component Cemented Surgical Technique, Zimmer, Inc., 2005, 2006, 2008, 2009, 2010, 16 pages.

* cited by examiner

*Primary Examiner* — Kevin T Truong
*Assistant Examiner* — Christian Sevilla
(74) *Attorney, Agent, or Firm* — Schwegman, Lundberg & Woessner P.A.

(57) ABSTRACT

A surgical instrument including a cutting instrument for shaping a bone as well as an impaction/extraction device for use with the cutting instrument is disclosed.

19 Claims, 5 Drawing Sheets

SURGICAL INSTRUMENT FOR IMPACTING AND EXTRACTING A CUTTING INSTRUMENT

BACKGROUND

1. Technical Field

The present disclosure relates to surgical instruments, and, more particularly, to surgical instruments for preparing the proximal end of a tibia for receiving a tibial prosthesis.

2. Description of the Related Art

Orthopaedic prostheses are commonly utilized to repair and/or replace damaged bone and tissue in the human body. For example, a knee prosthesis used in total knee arthroplasty may include a tibial base plate that is affixed to a resected or natural proximal tibia, a femoral component attached to a resected or natural distal femur, and a tibial bearing component coupled with the tibial base plate and disposed between the base plate and femoral component. Prostheses frequently seek to provide articulation similar to a natural, anatomic articulation of a knee joint, including providing a wide range flexion.

To prepare the relevant bones of the human body to receive prosthetic components, a variety of cutting instruments are sometimes utilized. In the case of the proximal tibia, a bone saw may be utilized to prepare a planar osteotomy of the proximal tibia which is then followed by drilling of the intramedullary canal of the tibia to accommodate a stem extending from the base plate of a tibial prosthesis. Many tibial prostheses include a keel extending from opposing sides of the stem of the tibial prosthesis. To further shape the tibia to receive the tibial keel, a broach is impacted into the proximal surface of the tibia to create a cavity sized to receive the keel of the tibial prosthesis. After impacting the broach, it must be extracted from the tibia while maintaining the shape of the cavity formed thereby.

When preparing the proximal tibia to receive a tibial prosthesis, instrumentation including a sizing plate may be utilized to facilitate forming a cavity in the tibia sized and shaped to accommodate the stem and keel of a tibial prosthesis that is properly positioned and oriented. The size of the sizing plate corresponds to the size of a prosthesis which is to be mated to the bone. The sizing plate is positioned atop the proximal tibia after the initial, planar osteotomy is performed. Positioning of the sizing plate provides an indication of the location and orientation of the final prosthesis and guides the location of the subsequent bone shaping steps, i.e., drilling and broaching, which are utilized to prepare the bone to receive the tibial prosthesis.

SUMMARY

The present disclosure provides a surgical instrument including a cutting instrument for shaping a bone as well as an impaction/extraction device for use with the cutting instrument. The impaction/extraction device includes a housing having an internal wall defining a longitudinal cannula and a central shaft positioned in the longitudinal cannula of the housing. The central shaft is moveable longitudinally within the longitudinal cannula of the housing. The central shaft is secured or releasably securable to the cutting instrument so that reciprocation of the central shaft within the housing can cause the cutting instrument to, alternatively, be impacted into or extracted from a bone. An extraction lever is pivotally connected to the housing and presents a proximally facing impaction surface adjacent to an impaction surface formed on a proximal end of the central shaft. The impaction surface formed on the proximal end of the central shaft is also proximally facing. With this configuration, impaction of the impaction surface of the central shaft as well as impaction of the impaction surface of the extraction lever can be done by impacting or striking these surfaces with a mallet in a proximal to distal motion. The extraction lever includes an extraction arm opposite the extraction lever and impaction surface, with the extraction arm positionable into contact with a distal facing extraction surface formed on the central shaft. In this configuration, impaction of the extraction lever impaction surface positions the extraction arm in contact with the extraction surface of the central shaft and applies a distal to proximal force to the central shaft to effect extraction of a tibial broach which has previously been impacted into the tibia.

The extraction lever impaction surface may be curved to facilitate impaction of the same with a mallet moving in a proximal to distal direction relative to the instrument. Specifically, as the extraction lever articulates to effect extraction of the broach from the tibia, the curved surface ensures that no matter the rotational position of the extraction lever, the extraction lever impaction surface presents a proximally facing surface transverse to the longitudinal axis of the central shaft. Specifically, the extraction lever impaction surface of this form of the present invention defines a curve in a plane containing the longitudinal axis of the central shaft and is substantially linear in a direction perpendicular to that plane. For the purposes of this description, substantially linear is meant to encompass deviations from linear within manufacturing tolerances. With respect to the surgical instrument of the present disclosure, "proximal" and "distal" are used with reference to a user of the instrument. Specifically, "proximal" denotes a position of the instrument closest to a user of the instrument, while "distal" refers to a portion of the instrument furthest from the user during use of the instrument.

When used in combination with a support structure such as a tibial sizing plate, the surgical instrument of the present invention may incorporate at least one magnet positioned to attract the support structure to the housing of the surgical instrument as the support structure is indexed to the surgical instrument. Embodiments of the surgical instrument of the present invention may further include a ball detent or spring clip operable to hold the central shaft in a retracted position relative to the housing. The ball detent of this form of the present invention is useful in retracting the cutting instrument from the distal extent of the housing so that the surgical instrument can be secured to a support structure without interference from the cutting instrument.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein describe and illustrate exemplary embodiments of the invention, and such exemplifications are not to be construed as limiting the scope of the invention in any manner.

DETAILED DESCRIPTION

Figure 1:
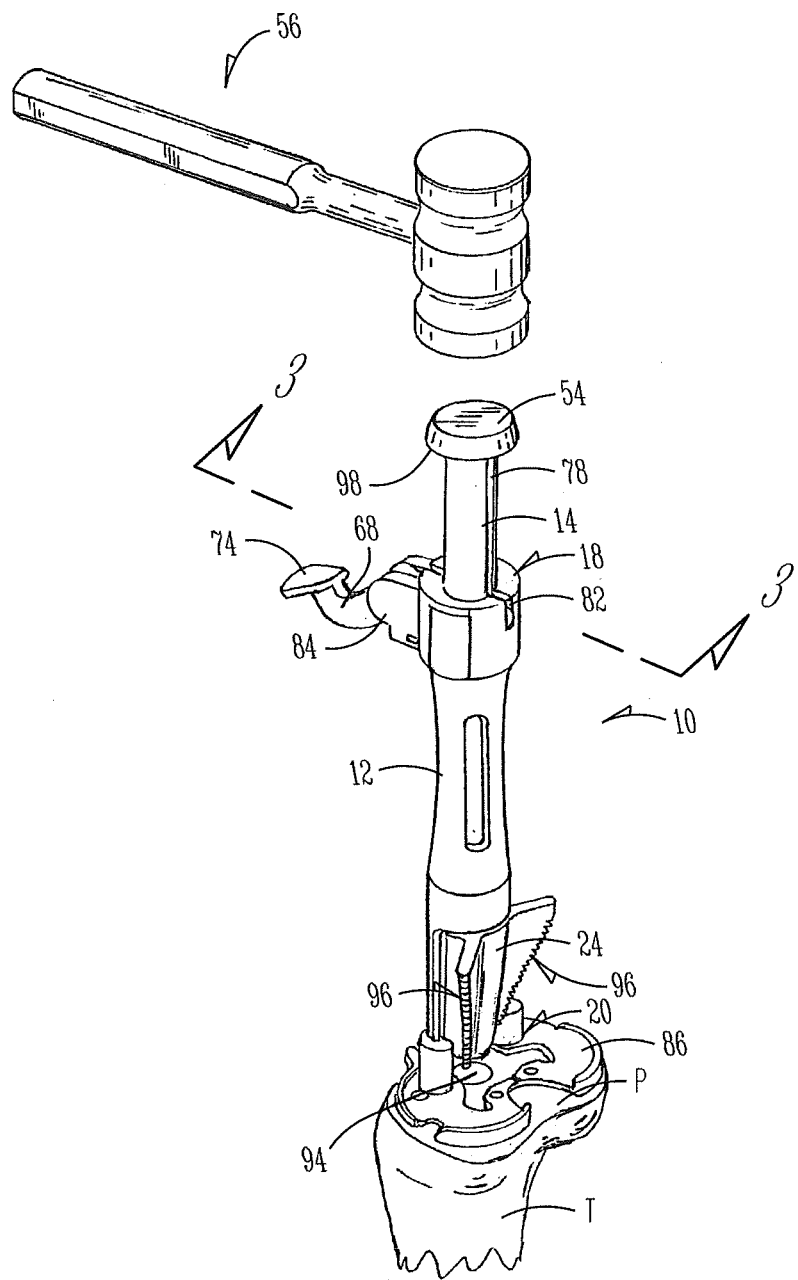
FIG. 1 is a perspective view of a surgical instrument in accordance with the present invention.
Figure 2:
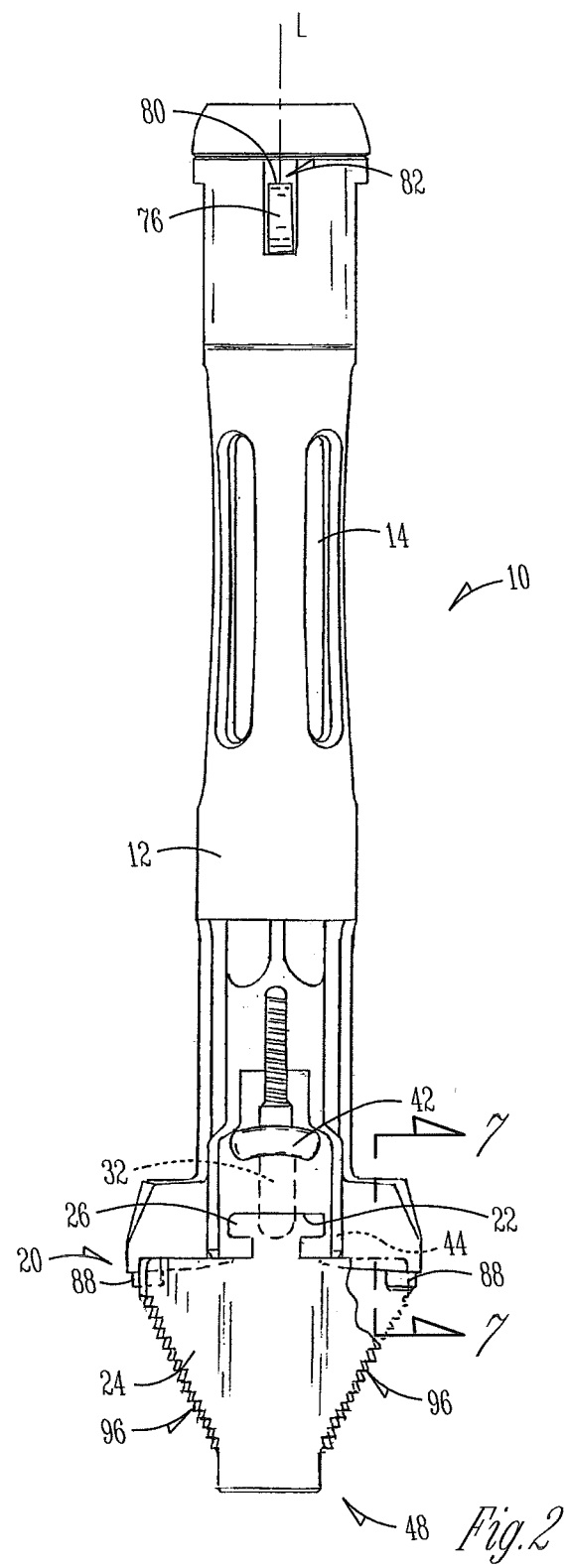
FIG. 2 is a radial elevational view of impaction/extraction instrument in accordance with the present invention.
Figure 3:
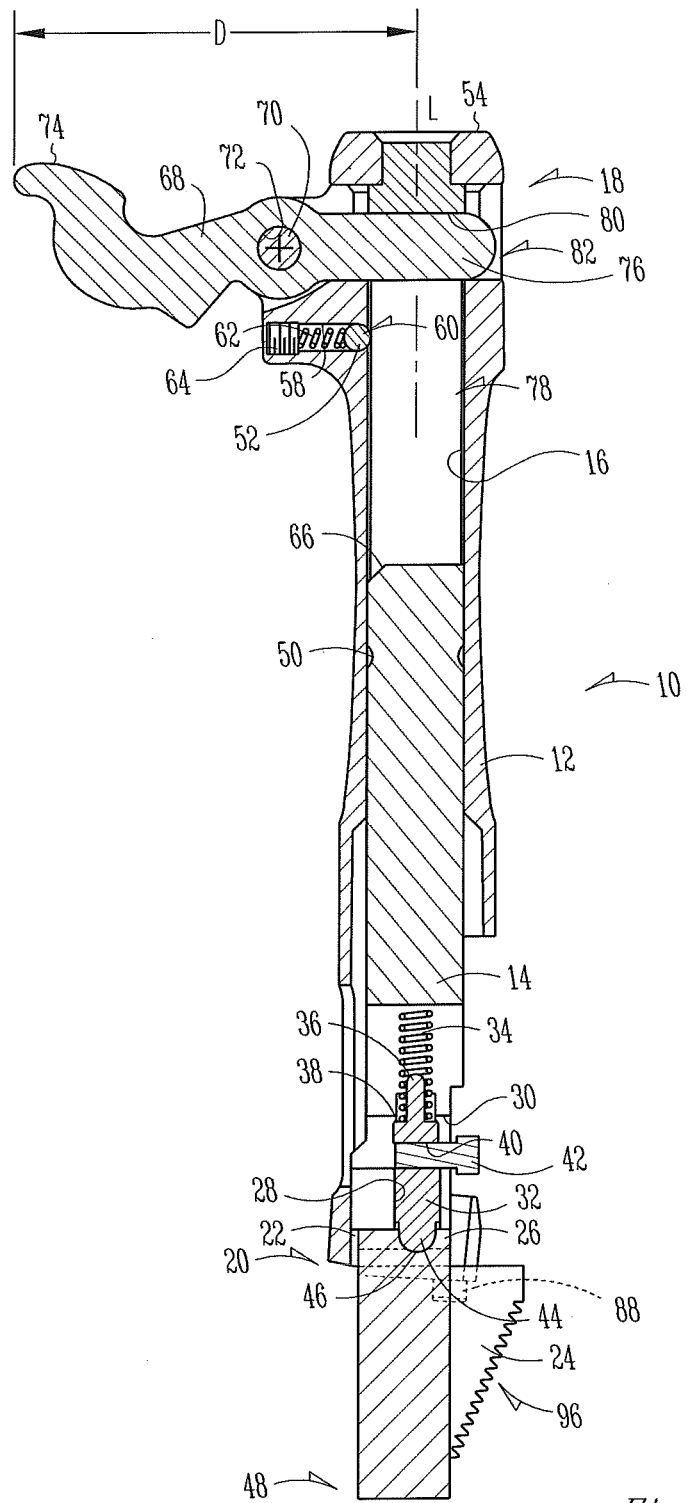
FIG. 3 is a cross-sectional view of the instrument illustrated in FIGS. 1 and 2 taken along lines 3-3 of FIG. 1.

Referring to FIGS. 1-3, impaction/extraction instrument 10 includes housing 12 and central shaft 14. Referring to FIG. 3, housing 12 includes internal wall 16 defining a longitudinal cannula spanning proximal end 18 and distal end 20 of housing 12. As illustrated in FIG. 3, central shaft 14 is positioned within the cannula formed by internal wall 16. Internal wall 16 of housing 12 and the exterior of central shaft 14 have complementary geometries, e.g., circular geometries, which allow for axial reciprocation of central shaft 14 along its longitudinal axis L relative to housing 12. Tibial broach 24 is secured to a distal end of central shaft 14.

Referring to FIGS. 2 and 3, central shaft 14 includes internal wall 22 defining a T-shaped recess at a distal end of central shaft 14. As illustrated in FIG. 3, internal wall 22 of central shaft 14 extends perpendicular to longitudinal axis L of central shaft 14 such that the T-shaped recess formed by internal wall 22 of central shaft 14 is perpendicular to the longitudinal axis L of central shaft 14. Referring to FIG. 2, tibial broach 24 includes T-shaped protrusion 26 at a proximal end thereon. T-shaped protrusion 26 has a complimentary geometry to the geometry of the T-shaped recess formed by internal wall 22 of central shaft 14. Specifically, T-shaped recess 26 is substantially congruent to the T-shaped recess formed by internal wall 22 of central shaft 14 and is sized such that a close fit can be formed therebetween. Referring to FIG. 3, central shaft 14 includes longitudinal bore 28 which is intersected by transverse bore 30. Longitudinal bore 28 is sized to receive locating pin 32 as well as spring 34. As illustrated in FIG. 3, longitudinal bore 28 is exemplified as a stepped bore having a smaller diameter portion receiving spring 34 and a larger diameter portion receiving locating pin 32. Locating pin 32 includes proximal protrusion 36 which terminates distally at shoulder 38. Proximal protrusion 36 is sized to be received within the interior of spring 34. Shoulder 38 has a radial expanse greater than the radial expanse of spring 34 so that spring 34 rests against shoulder 38. Locating pin 32 includes transverse bore 40 into which button 42 is positioned. Button 42 is secured to locating pin 32 so that movement of button 42 effects movement of locating pin 32. As illustrated in FIG. 3, spring 34 biases locating pin 32 distally such that button 42 abuts the distal portion of the wall forming transverse bore 30.

At its distal end, locating pin 32 includes spherical distal end 44. As illustrated in FIG. 3, spherical distal end 44 projects into the T-shaped recess defined by internal wall 22 of central shaft 14 in the normally biased position of locating pin 32. Spherical end 44 of locating pin 32 may be withdrawn from the T-shaped recess formed by internal wall 22 of central shaft 14 by actuating button 42 proximally so that locating pin 32 is moved against the spring biasing force of spring 34.

To operably secure tibial broach 24 to impaction/extraction instrument 10, button 42 is actuated proximally against the spring biasing force of spring 34 to withdraw spherical distal end 44 of locating pin 32 from the T-shaped recess defined by internal wall 22 of central shaft 14. With spherical distal end 44 of locating pin 32 withdrawn from the T-shaped recess, T-shaped protrusion 26 of tibial broach 24 can be positioned within the T-shaped recess formed by internal wall 22 of central shaft 14. In this position, actuation of button 42 may cease so that spring 34 biases locating pin 32 downwardly and spherical distal end 44 of locating pin 32 is positioned within divot 46 formed in a proximal end of tibial broach 24.

With tibial broach 24 secured to impaction/extraction instrument 10, the central shaft 14 can be pulled proximally relative to housing 12 to move tibial broach 24 proximally relative to housing 12 such that distal end 48 of tibial broach 24 does not extend distally from distal end 20 of housing 12. In this way, the distal most extent of tibial broach 24 will not extend beyond the distal most extent of housing 12 and, therefore, securement of impaction/extraction instrument 10 to a support structure, as will be further described hereinbelow, will not be interfered with by tibial broach 24. To hold tibial broach 24 in this retracted position, central shaft 14 includes divot 50 sized to receive ball 52 of a ball detent mechanism. As illustrated in FIG. 3, divot 50 can take the form of an annular groove extending about the circumference of central shaft 14. With tibial broach 24 in the withdrawn position, ball 52 engages divot 50 to hold tibial broach in a position such that it does not extend beyond distal end 20 of housing 12. Divot 50 may, in alternative embodiments, comprise a spherical divot sized to receive ball 52. To move tibial broach 24 from this position, impaction surface 54 may be impacted by mallet 56 (FIG. 1).

The ball detent mechanism utilized to hold tibial broach 24 in its withdrawn position includes transverse bore 58 intersecting internal wall 16 at opening 60. Opening 60 can be a circular opening having a diameter less than the diameter of ball 52. Positioned within transverse bore 58 is spring 62 and set screw 64. In an alternative embodiment, set screw 64 may be replaced with a cap which is welded in place within transverse boar 58. In the finally seated position of set screw 64 illustrated in FIG. 3, spring 62 is compressed against ball 52 such that ball 52 extends beyond opening 60 and into the longitudinal cannula defined by internal wall 16 of housing 12. As central shaft 14 is moved proximally, ramp 66 formed on central shaft 14 engages ball 52 so that ball 52 is moved against the biasing force of spring 62 and withdrawn from the cannula defined by internal wall 16 of housing 12. As central shaft 14 is moved further proximally such that ball 52 is aligned with divot 50, biasing force of spring 62 positions ball 52 in divot 50 as described hereinabove. The retracted position of tibial broach 24 is illustrated in FIG. 1.

A position of tibial broach 24 corresponding to its maximum extension distally from distal end 20 of housing 12 is illustrated in FIGS. 2 and 3. In this position, extraction lever 68 can be utilized to apply a distal to proximal force to central shaft 14 and move central shaft 14 and tibial broach 24 proximally. Extraction lever 68 is pivotally connected to housing 12 by cylindrical pivot pin 70. Cylindrical pivot pin 70 is pivotally received in a pivot aperture sized to allow rotation but not radial translation of cylindrical pivot pin 70 relative to the pivot aperture. In the embodiment illustrated in FIG. 3, extraction lever 68 includes cylindrical aperture 72 into which cylindrical pivot pin 70 is positioned. In this embodiment, cylindrical aperture 72 is sized to receive cylindrical pivot pin 70 to pivotally connect extraction lever 68 to housing 12, with cylindrical aperture 72 sized to allow rotation of extraction lever 68 relative to housing 12 but not to allow translation of extraction lever 68 in a direction oriented radially from cylindrical pivot pin 70. In alternative embodiments, cylindrical pivot pin 70 may be fixedly secured to extraction lever 68 but may be pivotally connected within a cylindrical aperture formed in yolk 84 (FIG. 1) in a similar fashion to the pivotal connection between cylindrical pivot pin 70 and cylindrical aperture 72 described above.

On opposing sides of cylindrical pivot pin 70, extraction lever 68 includes extraction lever impaction surface 74 and extraction arm 76. Extraction lever impaction surface 74 faces proximally, away from distal end 20 of housing 12. Because extraction lever impaction surface 74 faces proximally, it can be impacted by mallet 56 (FIG. 1) along a trajectory parallel to the impaction required to seat tibial broach 24, as will be further described hereinbelow.

Extraction arm 76 resides within slot 78 formed in central shaft 14. As illustrated in FIG. 3, slot 78 terminates proximally in extraction surface 80. Extraction surface 80 faces distally, away from impaction surface 54 which forms the proximal end of impaction/extraction instrument 10. With this arrangement, impaction of extraction lever impaction surface 74 with mallet 56 positions extraction arm 76 to contact extraction surface 80 and apply a distal to proximal force to central shaft 14 which will tend to pull tibial broach 24 proximally from the position illustrated in FIG. 3 toward the withdrawn position illustrated in FIG. 1. Movement of extraction arm 76 relative to housing 12 is accommodated by slot 82 formed in housing 12.

Referring to FIG. 3, extraction lever impaction surface 74 has a radially outward most extent relative to longitudinal axis L of central shaft 14 illustrated as distance D. Distance D measures no more than 10 cm. With extraction lever impaction surface 74 spaced no more than 10 cm from longitudinal axis L of central shaft 14, the torque imparted to impaction/extraction instrument 10 when mallet 56 strikes extraction lever impaction surface is minimized and therefore toggling of tibial broach 24 within the broached bone will be minimized. Furthermore, the center of impaction surface 74 is spaced approximately 25 mm from the center of cylindrical pivot pin 70. With an expected impaction force on the extraction head of approximately 7 kN, this would result in a torque about the center of cylindrical pivot pin 70 of about (7,000 N)×(0.025 m)=175 Nm. The inventors of the present invention have concluded that a torque of less than 300 Nm is desired to prevent toggling of tibial broach 24 during extraction thereof. In certain embodiments of the present invention, distance D can be as little as 5 cm. In alternative embodiments of the present invention, distance D can be any value between 5 and 10 cm in 0.5 cm increments, i.e., 5.0, 5.5, 6.0, 6.5, 7.0, 7.5, 8.0, 8.5, 9.0, 9.5 or 10.0 cm.

In an exemplary embodiment of the present invention, the lever ratio of the extraction lever is approximately 1.6:1. What this means is that the length of the arm extending from the center of cylindrical pivot pin 70 to a terminal end of extraction lever 68 adjacent to extraction lever impaction surface 74 is approximately 1.6 times the length of extraction arm 76 from the center of cylindrical pivot pin 70 to a second terminal end of extraction lever 68 on extraction arm 76. The inventors of the present application have determined that a lever ratio of extraction lever 68 anywhere between 3:1 to 1:1 strikes an appropriate balance between decreasing toggling of tibial broach 24 during extraction while also providing an instrument actuateable with a comfortable amount of force applied by the user.

Figure 5:
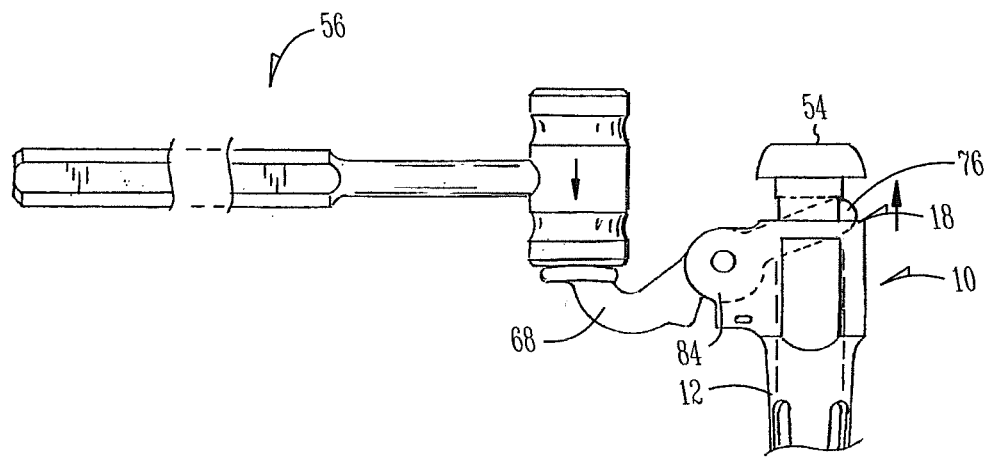
FIG. 5 is a partial view of the impaction/extraction instrument illustrated in FIGS. 1-3, illustrating use of the same to extract a cutting instrument.

Extraction lever impaction surface 74 defines a curve in a plane containing the longitudinal axis of central shaft 14. The section plane along which FIG. 3 is taken is such a plane. As illustrated in FIG. 3, extraction lever impaction surface 74 is curved in a plane containing longitudinal axis L of central shaft 14. While extraction lever impaction surface 74 is curved in a plane containing longitudinal axis L of central shaft 14, it is substantially linear in a direction perpendicular to such plane. "Substantially linear" is meant to encompass linear configurations and those configurations within manufacturing tolerances of being linear. What this means is that in planes parallel to the plane along which the cross-sectional view of FIG. 3 is taken, the profile of extraction lever impaction surface 74 remains unchanged. Curving of extraction lever impaction surface 74 facilitates articulation of extraction lever 68 by impacting extraction lever impaction surface 74 with mallet 56. Specifically, the curvature of extraction lever impaction surface 74 means that mallet 56 can be actuated in a proximal to distal direction d as illustrated in FIG. 5 while maintaining good contact with extraction lever impaction surface 74 throughout a full range of motion of extraction lever 68.

Referring to FIG. 1, impaction/extraction instrument 10 can be utilized to broach tibia T in the following manner. After initially osteotomizing proximal surface P of tibia T, tibial sizing plate 86 is chosen, oriented with respect to tibial T and secured thereto. Techniques for osteotomizing proximal surface P of tibia T can include securing a cut guide to tibia T which guides an oscillating saw to cut proximal tibia T. Examples of such techniques can be found in the Zimmer NexGen LPS Fixed Knee Surgical Technique bearing copyright dates of 2002, 2008, the entire disclosure of which is hereby explicitly incorporated by reference herein. Alternative techniques for osteotomizing the proximal tibia and utilizing a sizing plate can be found in the Zimmer NexGen CR Flex and LPS Flex Knees Surgical Technique with posterior referencing instrumentation bearing copyright dates of 2010, 2011 and the Zimmer NexGen MIS Tibial Component Cemented Surgical Technique bearing copyright dates of 2005, 2006, 2008, 2009 and 2010, the entire disclosures of which are hereby explicitly incorporated by reference herein. Additionally, preparation of a tibia to receive a tibial prosthesis is shown and described in U.S. Pat. No. 5,634,927, assigned to the assignee of the present disclosure, the entire disclosure of which is hereby explicitly incorporated by reference herein.

Figure 6:
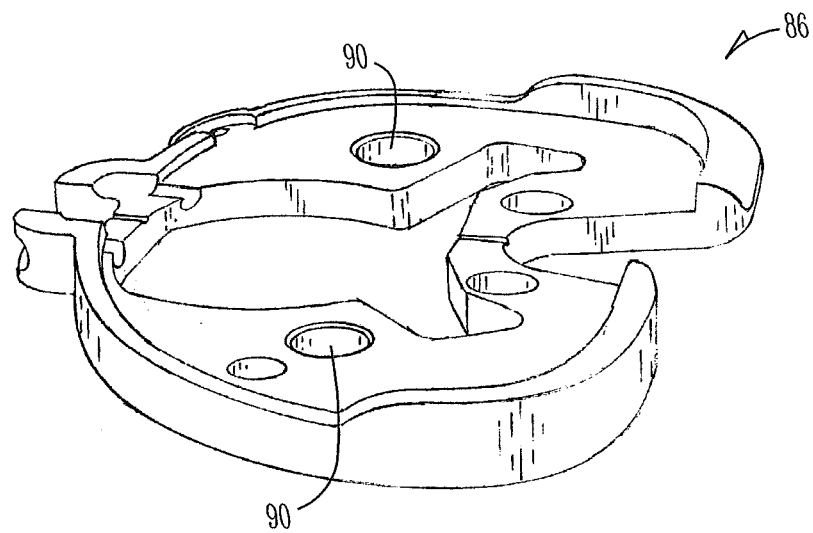
FIG. 6 is a perspective view of a tibial sizing plate useable to guide the impaction/extraction instrument of the present invention.
Figure 7:
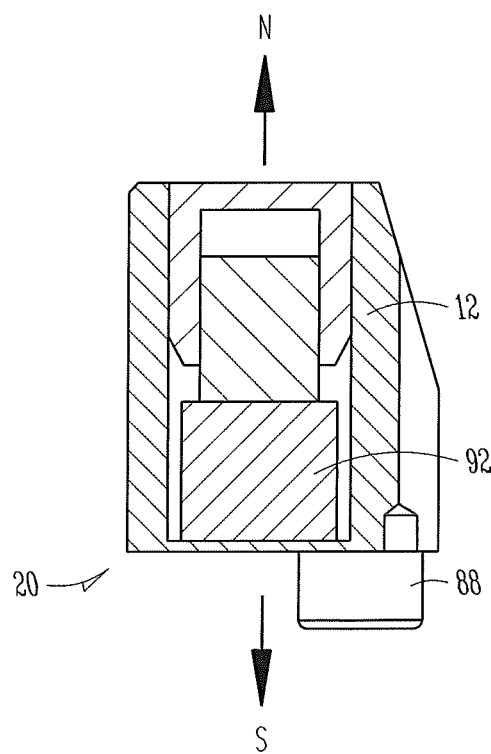
FIG. 7 is a sectional view illustrating a magnetic securement mechanism in accordance with the present invention.

After pinning tibial sizing plate 86 to tibia T, impaction/extraction instrument 10 can be indexed to tibial sizing plate 86 so that impaction/extraction instrument 10 is supported and guided by tibial sizing plate 86. Referring to FIGS. 2 and 7, impaction/extraction instrument 10 includes bosses 88 extending distally from distal ends 20 of housing 12. Bosses 88 are sized, shaped and spaced to cooperate with apertures 90 (FIG. 6) in tibial sizing plate 86 to index impaction/extraction instrument 10 to tibial sizing plate 86. In a portion of housing 12 adjacent to each boss 88, a chamber holds a magnet 92 as illustrated in FIG. 7. Magnets 92 are oriented relative to their respective bosses 88 such that when each boss 88 is positioned within an aperture 90 to index impaction/extraction instrument 10 to tibial sizing plate 86, magnet 92 will be positioned over a proximal surface of tibial base plate 86. When using a metallic base plate 86, magnets 92 will draw tibial sizing plate 86 toward impaction/extraction instrument 10 and facilitate indexing of impaction/extraction instrument 10 to tibial sizing plate 86. During this process of indexing impaction/extraction instrument 10 to tibial sizing plate 86, tibial broach 24 can maintain the extracted position illustrated in FIG. 1 so that it cannot interfere with the indexing process.

Figure 4:
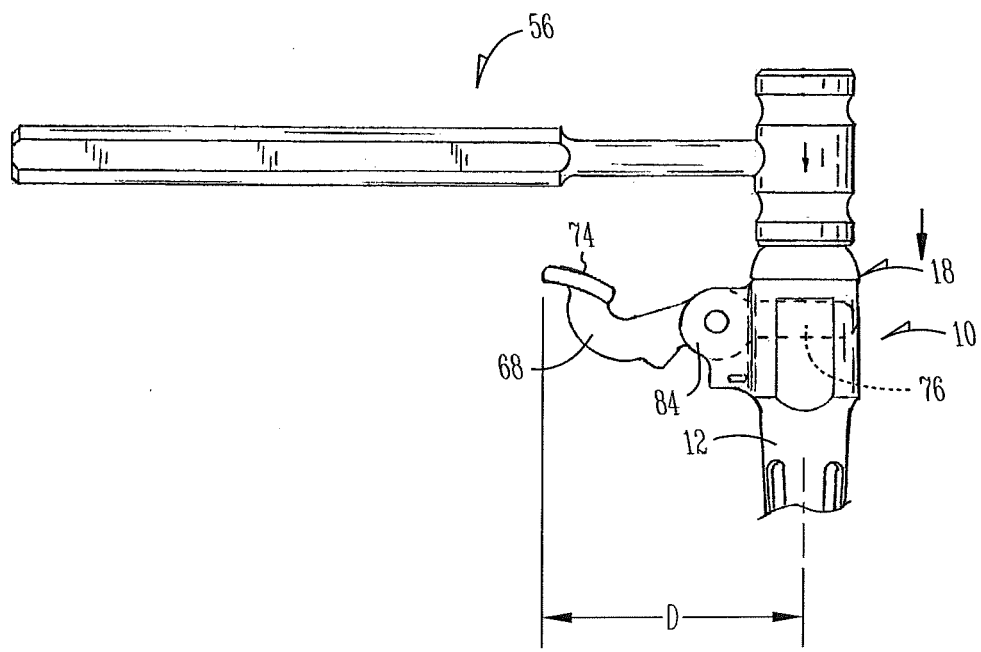
FIG. 4 is a partial view of the impaction/extraction instrument illustrated in FIGS. 1-3, illustrating use of the same to impact a cutting instrument.

With impaction/extraction instrument 10 properly indexed to tibial sizing plate 86, mallet 56 may be utilized to strike impaction surface 54 to seat tibial broach 24 in tibia T and create an aperture in tibia T sized to accommodate the keel of a tibial prosthesis. Specifically, while using one hand to grasp housing 12, a surgeon may use his or her other hand to actuate mallet 56 so that its head collides with impaction surface 54 to impact the impaction surface and effect seating of tibial broach 24 in tibia T. Prior to broaching tibia T, aperture 94 may be formed in tibia T to accommodate distal end 48 of tibial broach 24. As distal end 48 of tibial broach 24 enters aperture 94, teeth 96 of tibial broach 24 contact the bone of tibia T and effect cutting of the same. Final seating of tibial broach 24 is signaled when undersurface 98 opposing impaction surface 54 contacts proximal end 18 of housing 12 as illustrated in FIGS. 3 and 4. In this position, mallet 56 may be utilized to provide an impaction force to extraction lever impaction surface 74 as illustrated in FIG. 5. Such impaction force creates a torque about the center of cylindrical pivot pin 70 (FIG. 3) and generates an extraction force in a distal to proximal direction along longitudinal axis L of central shaft 14.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical instrument, comprising:
   a cutting instrument for shaping a bone wherein said cutting instrument comprises a tibial broach;
   a housing having an internal wall defining a longitudinal cannula;
   a central shaft positioned in said longitudinal cannula of said housing, said central shaft having a longitudinal axis, said central shaft moveable within said longitudinal cannula of said housing relative to said housing along said longitudinal axis of said central shaft, said central shaft having a proximal end and a distal end securable to said cutting instrument;
   an impaction surface facing proximally, away from a distal end of the surgical instrument, said impaction surface forming said proximal end of said central shaft, whereby impacting said impaction surface applies a proximal to distal force to said central shaft;
   an extraction lever pivotally connected to said housing, said extraction lever having an extraction lever impaction surface facing proximally, away from a distal end of the surgical instrument, said extraction lever impaction surface moveable relative to said central shaft, said extraction lever having an extraction arm opposite said extraction lever impaction surface, said central shaft having an extraction surface facing distally away from a proximal end of the surgical instrument, said extraction arm positionable to contact said extraction surface, whereby impacting said extraction lever impaction surface positions said extraction arm in contact with said extraction surface and applies a distal to proximal force to said central shaft.

2. The surgical instrument of claim 1, wherein said extraction lever impaction surface defines a curve in a plane containing the longitudinal axis of the central shaft, said impaction surface being substantially linear in a direction perpendicular to said plane.

3. A combination, comprising the surgical instrument of claim 1 and a metallic support structure having a support structure indexing feature, said housing having a housing indexing feature, said support structure indexing feature and said housing indexing feature selectably engageable to index the surgical instrument to the support structure, said housing incorporating at least one magnet positioned to attract said metallic support structure to said housing as said housing indexing feature in brought into engagement with said support structure indexing feature.

4. The combination of claim 3, wherein said support structure comprises a tibial sizing plate.

5. The surgical instrument of claim 1, wherein said housing includes a transverse bore intersecting said longitudinal cannula of said housing at an opening, said surgical instrument further comprising:
   a ball detent positioned in said transverse bore and extending into said longitudinal cannula of said housing, said ball detent having a diameter larger than a diameter of said opening;
   a spring positioned in said transverse bore and biasing said ball detent toward said opening;
   said central shaft including a divot sized to receive said ball detent, whereby, with said ball detent positioned in said divot, movement of said central shaft relative to said housing is resisted, whereby, with said cutting instrument secured to said central shaft and with said ball detent positioned in said divot, said cutting instrument does not extend distally beyond a distal extent of said housing.

6. The surgical instrument of claim 1, wherein said extraction lever impaction surface is spaced no more than 10 cm from said longitudinal axis of said central shaft.

7. The surgical instrument of claim 1, further comprising:
   a cylindrical pivot pin pivotally received in a pivot aperture sized to allow rotation but not radial translation of said cylindrical pivot pin relative to said pivot aperture, said cylindrical pivot pin pivotally connecting said extraction lever to said housing.

8. The surgical instrument of claim 7, wherein said extraction lever extends a first distance from a center of said cylindrical pivot pin to a first terminal end of the extraction lever adjacent to the extraction lever impaction surface and said extraction lever extends a second distance from said center of said cylindrical pivot pin to a second terminal end of the extraction lever on the extraction arm, a ratio of said first distance to said second distance being in the range of 3:1 to 1:1.

9. The surgical instrument of claim 8, wherein said ratio of said first distance to said second distance equals 1.6:1.

10. The surgical instrument of claim 1, wherein said distal end of said central shaft includes a central shaft securement feature, said cutting instrument including a cutting instrument securement feature matable with said central shaft securement feature to releasably secure said cutting instrument to said central shaft.

11. The surgical instrument of claim 10, wherein said central shaft securement feature comprises a wall defining a T-shaped recess and a locating pin having a spherical distal end, said locating pin moveable within said T-shaped recess, and said cutting instrument securement feature comprises a T-shaped protrusion shaped to be received within said T-shaped recess of said central shaft and a divot sized to receive said spherical distal end of said locating pin, whereby, with said T-shaped protrusion positioned in said T-shaped recess and said spherical distal end of said locating pin positioned in said divot, movement of said cutting instrument relative to said central shaft is resisted.

12. A surgical instrument, comprising:
   a cutting instrument for shaping a bone wherein said cutting instrument comprises a tibial broach;
   a housing having an internal wall defining a longitudinal cannula;
   a central shaft positioned in said longitudinal cannula of said housing, said central shaft having a longitudinal axis, said central shaft moveable within said longitudinal cannula of said housing relative to said housing along said longitudinal axis of said central shaft, said central shaft having a proximal end and a distal end securable to said cutting instrument;
   an impaction surface facing proximally, away from a distal end of the surgical instrument, said impaction surface forming said proximal end of said central shaft, whereby impacting said impaction surface applies a proximal to distal force to said central shaft;
   an extraction lever pivotally connected to said housing, said extraction lever having an extraction lever impaction surface facing proximally away from a distal end of the surgical instrument, said extraction lever impaction surface defining a curve in a plane containing the longitudinal axis of the central shaft, said impaction surface being substantially linear in a direction perpendicular to said plane, said extraction lever having an extraction arm opposite said extraction lever impaction surface, said central shaft having an extraction surface facing distally, away from a proximal end of the surgical instrument, said extraction arm positionable to contact said extraction surface, whereby impacting said extraction lever impaction surface positions said extraction arm in contact with said extraction surface and applies a distal to proximal force to said central shaft.

13. A combination, comprising the surgical instrument of claim 12 and a metallic support structure having a support structure indexing feature, said housing having a housing indexing feature, said support structure indexing feature and said housing indexing feature selectably engageable to index the surgical instrument to the support structure, said housing incorporating at least one magnet positioned to attract said metallic support structure to said housing as said housing indexing feature in brought into engagement with said support structure indexing feature.

14. The combination of claim 13, wherein said support structure comprises a tibial sizing plate.

15. The surgical instrument of claim 12, wherein said housing includes a transverse bore intersecting said longitudinal cannula of said housing at an opening, said surgical instrument further comprising:
   a ball detent positioned in said transverse bore and extending into said longitudinal cannula of said housing, said ball detent having a diameter larger than a diameter of said opening;
   a spring positioned in said transverse bore and biasing said ball detent toward said opening;
   said central shaft including a divot sized to receive said ball detent, whereby, with said ball detent positioned in said divot, movement of said central shaft relative to said housing is resisted, whereby, with said cutting instrument secured to said central shaft and with said ball detent positioned in said divot, said cutting instrument does not extend distally beyond a distal extent of said housing.

16. The surgical instrument of claim 12, wherein said extraction lever impaction surface is spaced no more than 10 cm from said longitudinal axis of said central shaft.

17. The surgical instrument of claim 12, further comprising:
   a cylindrical pivot pin pivotally received in a pivot aperture sized to allow rotation but not radial translation of said cylindrical pivot pin relative to said pivot aperture, said cylindrical pivot pin pivotally connecting said extraction lever to said housing.

18. The surgical instrument of claim 12, wherein said extraction lever extends a first distance from a center of said cylindrical pivot pin to a first terminal end of the extraction lever adjacent to the extraction lever impaction surface and said extraction lever extends a second distance from said center of said cylindrical pivot pin to a second terminal end of the extraction lever on the extraction arm, a ratio of said first distance to said second distance being in the range of 3:1 to 1:1.

19. The surgical instrument of claim 18, wherein said ratio of said first distance to said second distance equals 1.6:1.

* * * * *